United States Patent
Tokarz et al.

(10) Patent No.: US 12,268,414 B2
(45) Date of Patent: Apr. 8, 2025

(54) RETENTION ANCHOR FOR SURGICAL ACCESS DEVICES

(71) Applicant: Covidien LP, Mansfield, MA (US)

(72) Inventors: Christopher A. Tokarz, Torrington, CT (US); Kevin Desjardin, Prospect, CT (US); Oksana Buyda, East Haven, CT (US); Douglas M. Pattison, East Hartford, CT (US); Amanda M. Adinolfi, Wallingford, CT (US); Astley C. Lobo, West Haven, CT (US)

(73) Assignee: Covidien LP, Mansfield, MA (US)

( * ) Notice: Subject to any disclaimer, the term of this patent is extended or adjusted under 35 U.S.C. 154(b) by 1006 days.

(21) Appl. No.: 16/802,077

(22) Filed: Feb. 26, 2020

(65) Prior Publication Data

US 2021/0259731 A1    Aug. 26, 2021

(51) Int. Cl.
*A61B 17/34*    (2006.01)

(52) U.S. Cl.
CPC .. *A61B 17/3423* (2013.01); *A61B 2017/3484* (2013.01)

(58) Field of Classification Search
CPC ........ A61B 17/3423; A61B 2017/3484; A61B 2017/348–3492; A61B 17/3498; A61B 2017/3419; A61M 2039/0223; A61M 2039/0261
See application file for complete search history.

(56) References Cited

U.S. PATENT DOCUMENTS

| | | |
|---|---|---|
| 397,060 A | 1/1889 | Knapp |
| 512,456 A | 1/1894 | Sadikova |
| 1,213,005 A | 1/1917 | Pillsbury |
| 2,912,981 A | 11/1959 | Keough |
| 2,936,760 A | 5/1960 | Gains |
| 3,039,468 A | 6/1962 | Price |
| 3,050,066 A | 8/1962 | Koehn |

(Continued)

FOREIGN PATENT DOCUMENTS

| | | |
|---|---|---|
| EP | 0480653 A1 | 4/1992 |
| EP | 0610099 A2 | 8/1994 |

(Continued)

OTHER PUBLICATIONS

Extended European Search Report issued in corresponding European Application No. 21159215.9 dated Jun. 30, 2021, 8 pages.

*Primary Examiner* — Katherine H Schwiker
*Assistant Examiner* — Zehra Jaffri
(74) *Attorney, Agent, or Firm* — Draft Masters IP, LLC

(57) ABSTRACT

A surgical access assembly includes a cannula including an elongated shaft and a retention anchor movable position along the elongated shaft. The retention anchor includes an annular body and a wiper disposed at a distal end of the annular body. The annular body includes a proximally-facing surface, a distally-facing surface, an outer side surface, and an inner side surface. The inner side surface defines a channel for reception and passage of the elongated shaft therethrough and the proximally-facing surface defines a proximal opening into the channel. The wiper extends radially inwardly of the inner side surface and defines a distal opening into the channel for establishing a sealed relation about the elongated shaft. The distal opening has a smaller diameter than the proximal opening.

17 Claims, 3 Drawing Sheets

(56) References Cited

U.S. PATENT DOCUMENTS

| | | | |
|---|---|---|---|
| 3,253,594 A | 5/1966 | Matthews et al. | |
| 3,397,699 A | 8/1968 | Kohl | |
| 3,545,443 A | 12/1970 | Ansari et al. | |
| 3,713,447 A | 1/1973 | Adair | |
| 3,774,596 A | 11/1973 | Cook | |
| 3,800,788 A | 4/1974 | White | |
| 3,882,852 A | 5/1975 | Sinnreich | |
| 3,896,816 A | 7/1975 | Mattler | |
| 3,961,632 A | 6/1976 | Moossun | |
| RE29,207 E | 5/1977 | Bolduc et al. | |
| 4,083,369 A | 4/1978 | Sinnreich | |
| 4,217,889 A | 8/1980 | Radovan et al. | |
| 4,243,050 A | 1/1981 | Littleford | |
| 4,276,874 A | 7/1981 | Wolvek et al. | |
| 4,312,353 A | 1/1982 | Shahbabian | |
| 4,327,709 A | 5/1982 | Hanson et al. | |
| 4,345,606 A | 8/1982 | Littleford | |
| 4,411,654 A | 10/1983 | Boarini et al. | |
| 4,416,267 A | 11/1983 | Garren et al. | |
| 4,490,137 A | 12/1984 | Moukheibir | |
| 4,496,345 A | 1/1985 | Hasson | |
| 4,574,806 A | 3/1986 | McCarthy | |
| 4,581,025 A | 4/1986 | Timmermans | |
| 4,596,554 A | 6/1986 | Dastgeer | |
| 4,596,559 A | 6/1986 | Fleischhacker | |
| 4,608,965 A | 9/1986 | Anspach, Jr. et al. | |
| 4,644,936 A | 2/1987 | Schiff | |
| 4,653,477 A * | 3/1987 | Akui | A61B 1/00137 128/912 |
| 4,654,030 A | 3/1987 | Moll et al. | |
| 4,685,447 A | 8/1987 | Iversen et al. | |
| 4,701,163 A | 10/1987 | Parks | |
| 4,738,666 A | 4/1988 | Fuqua | |
| 4,769,038 A | 9/1988 | Bendavid et al. | |
| 4,772,266 A | 9/1988 | Groshong | |
| 4,779,611 A | 10/1988 | Grooters et al. | |
| 4,784,133 A | 11/1988 | Mackin | |
| 4,793,348 A | 12/1988 | Palmaz | |
| 4,798,205 A | 1/1989 | Bonomo et al. | |
| 4,800,901 A | 1/1989 | Rosenberg | |
| 4,802,479 A | 2/1989 | Haber et al. | |
| 4,813,429 A | 3/1989 | Eshel et al. | |
| 4,840,613 A | 6/1989 | Balbierz | |
| 4,854,316 A | 8/1989 | Davis | |
| 4,861,334 A | 8/1989 | Nawaz | |
| 4,865,593 A | 9/1989 | Ogawa et al. | |
| 4,869,717 A | 9/1989 | Adair | |
| 4,888,000 A | 12/1989 | McQuilkin et al. | |
| 4,899,747 A | 2/1990 | Garren et al. | |
| 4,917,668 A * | 4/1990 | Haindl | F16L 37/38 604/167.03 |
| 4,931,042 A | 6/1990 | Holmes et al. | |
| 4,955,895 A | 9/1990 | Sugiyama et al. | |
| 5,002,557 A | 3/1991 | Hasson | |
| 5,009,643 A | 4/1991 | Reich et al. | |
| 5,030,206 A | 7/1991 | Lander | |
| 5,030,227 A | 7/1991 | Rosenbluth et al. | |
| 5,074,871 A | 12/1991 | Groshong | |
| 5,098,392 A | 3/1992 | Fleischhacker et al. | |
| 5,104,383 A | 4/1992 | Shichman | |
| 5,116,318 A | 5/1992 | Hillstead | |
| 5,116,357 A | 5/1992 | Eberbach | |
| 5,122,122 A | 6/1992 | Allgood | |
| 5,122,155 A | 6/1992 | Eberbach | |
| 5,137,512 A | 8/1992 | Burns et al. | |
| 5,141,494 A | 8/1992 | Danforth et al. | |
| 5,141,515 A | 8/1992 | Eberbach | |
| 5,147,302 A | 9/1992 | Euteneuer et al. | |
| 5,147,316 A | 9/1992 | Castillenti | |
| 5,147,374 A | 9/1992 | Fernandez | |
| 5,158,545 A | 10/1992 | Trudell et al. | |
| 5,159,925 A | 11/1992 | Neuwirth et al. | |
| 5,163,949 A | 11/1992 | Bonutti | |
| 5,176,692 A | 1/1993 | Wilk et al. | |
| 5,176,697 A | 1/1993 | Hasson et al. | |
| 5,183,463 A | 2/1993 | Debbas | |
| 5,188,596 A | 2/1993 | Condon et al. | |
| 5,188,630 A | 2/1993 | Christoudias | |
| 5,195,507 A | 3/1993 | Bilweis | |
| 5,201,742 A | 4/1993 | Hasson | |
| 5,201,754 A | 4/1993 | Crittenden et al. | |
| 5,209,725 A | 5/1993 | Roth | |
| 5,215,526 A | 6/1993 | Deniega et al. | |
| 5,222,970 A | 6/1993 | Reeves | |
| 5,226,890 A * | 7/1993 | Ianniruberto | A61B 17/34 604/174 |
| 5,232,446 A | 8/1993 | Arney | |
| 5,232,451 A | 8/1993 | Freitas et al. | |
| 5,234,454 A | 8/1993 | Bangs | |
| 5,250,025 A | 10/1993 | Sosnowski et al. | |
| 5,258,026 A | 11/1993 | Johnson et al. | |
| 5,263,944 A * | 11/1993 | Vidal | A61B 17/3462 604/167.01 |
| 5,269,753 A | 12/1993 | Wilk | |
| 5,290,249 A | 3/1994 | Foster et al. | |
| 5,308,327 A | 5/1994 | Heaven et al. | |
| 5,309,896 A | 5/1994 | Moll et al. | |
| 5,314,443 A | 5/1994 | Rudnick | |
| 5,318,012 A | 6/1994 | Wilk | |
| 5,330,497 A * | 7/1994 | Freitas | A61B 17/34 604/164.12 |
| 5,342,307 A | 8/1994 | Euteneuer et al. | |
| 5,342,315 A * | 8/1994 | Rowe | A61B 17/3462 604/167.06 |
| 5,346,504 A | 9/1994 | Ortiz et al. | |
| 5,359,995 A | 11/1994 | Sewell, Jr. | |
| 5,361,752 A | 11/1994 | Moll et al. | |
| 5,370,134 A | 12/1994 | Chin et al. | |
| 5,383,889 A | 1/1995 | Warner et al. | |
| 5,385,553 A * | 1/1995 | Hart | A61B 17/3462 604/167.03 |
| 5,397,311 A | 3/1995 | Walker et al. | |
| 5,402,772 A | 4/1995 | Moll et al. | |
| 5,407,433 A | 4/1995 | Loomas | |
| 5,431,173 A | 7/1995 | Chin et al. | |
| 5,445,615 A | 8/1995 | Yoon | |
| 5,456,673 A * | 10/1995 | Ziegler | A61B 17/3462 604/533 |
| 5,468,248 A | 11/1995 | Chin et al. | |
| 5,514,091 A | 5/1996 | Yoon | |
| 5,514,153 A | 5/1996 | Bonutti | |
| 5,540,658 A | 7/1996 | Evans et al. | |
| 5,540,711 A | 7/1996 | Kieturakis et al. | |
| 5,607,441 A | 3/1997 | Sierocuk et al. | |
| 5,607,443 A | 3/1997 | Kieturakis et al. | |
| 5,632,761 A | 5/1997 | Smith et al. | |
| 5,656,013 A | 8/1997 | Yoon | |
| 5,667,479 A | 9/1997 | Kieturakis | |
| 5,667,520 A | 9/1997 | Bonutti | |
| 5,704,372 A | 1/1998 | Moll et al. | |
| 5,707,382 A | 1/1998 | Sierocuk et al. | |
| 5,713,869 A | 2/1998 | Morejon | |
| 5,722,986 A | 3/1998 | Smith et al. | |
| 5,728,119 A | 3/1998 | Smith et al. | |
| 5,730,748 A | 3/1998 | Fogarty et al. | |
| 5,730,756 A | 3/1998 | Kieturakis et al. | |
| 5,738,628 A | 4/1998 | Sierocuk et al. | |
| 5,755,693 A | 5/1998 | Walker et al. | |
| 5,762,604 A | 6/1998 | Kieturakis | |
| 5,772,680 A | 6/1998 | Kieturakis et al. | |
| 5,779,728 A | 7/1998 | Lunsford et al. | |
| 5,797,947 A | 8/1998 | Mollenauer | |
| 5,803,901 A | 9/1998 | Chin et al. | |
| 5,807,338 A * | 9/1998 | Smith | A61B 17/3417 606/167 |
| 5,810,867 A | 9/1998 | Zarbatany et al. | |
| 5,814,060 A | 9/1998 | Fogarty et al. | |
| 5,836,913 A | 11/1998 | Orth et al. | |
| 5,836,961 A | 11/1998 | Kieturakis et al. | |
| 5,865,802 A | 2/1999 | Yoon et al. | |
| 5,893,866 A | 4/1999 | Hermann et al. | |
| 5,925,058 A | 7/1999 | Smith et al. | |

(56) References Cited

U.S. PATENT DOCUMENTS

| | | | |
|---|---|---|---|
| 6,228,061 B1* | 5/2001 | Flatland | A61B 17/3462 604/264 |
| 6,361,543 B1 | 3/2002 | Chin et al. | |
| 6,368,337 B1 | 4/2002 | Kieturakis et al. | |
| 6,375,665 B1 | 4/2002 | Nash et al. | |
| 6,379,372 B1 | 4/2002 | Dehdashtian et al. | |
| 6,423,036 B1* | 7/2002 | Van Huizen | A61B 17/3417 604/117 |
| 6,432,121 B1 | 8/2002 | Jervis | |
| 6,447,529 B2 | 9/2002 | Fogarty et al. | |
| 6,468,205 B1 | 10/2002 | Mollenauer et al. | |
| 6,506,200 B1 | 1/2003 | Chin | |
| 6,514,272 B1 | 2/2003 | Kieturakis et al. | |
| 6,517,514 B1 | 2/2003 | Campbell | |
| 6,527,787 B1 | 3/2003 | Fogarty et al. | |
| 6,540,764 B1 | 4/2003 | Kieturakis et al. | |
| 6,796,960 B2 | 9/2004 | Cioanta et al. | |
| 7,842,013 B2* | 11/2010 | Haberland | A61B 17/3462 604/167.03 |
| 8,062,305 B2* | 11/2011 | Wenchell | A61B 17/3421 600/184 |
| 8,262,568 B2* | 9/2012 | Albrecht | A61B 17/3423 600/206 |
| 8,454,645 B2 | 6/2013 | Criscuolo et al. | |
| 8,911,407 B2* | 12/2014 | Smith | H04L 41/5074 604/167.03 |
| 8,926,508 B2* | 1/2015 | Hotter | A61B 17/3421 600/207 |
| 9,668,723 B2* | 6/2017 | Keating | A61B 17/0469 |
| 10,463,395 B2* | 11/2019 | Reid | A61B 17/3423 |
| 10,675,056 B2* | 6/2020 | Tokarz | A61B 17/3474 |
| 2004/0167473 A1 | 8/2004 | Moenning | A61B 17/3496 604/247 |
| 2005/0251191 A1* | 11/2005 | Taylor | A61M 13/003 606/190 |
| 2006/0293702 A1* | 12/2006 | Buser | A61B 17/3496 606/185 |
| 2007/0088277 A1* | 4/2007 | McGinley | A61M 13/003 604/167.01 |
| 2007/0213675 A1* | 9/2007 | Albrecht | A61B 17/3421 604/264 |
| 2007/0255218 A1* | 11/2007 | Franer | A61B 17/3462 604/167.02 |
| 2009/0182282 A1* | 7/2009 | Okihisa | A61B 17/3423 604/165.01 |
| 2010/0094228 A1* | 4/2010 | Bettuchi | A61B 17/3498 604/167.03 |
| 2010/0262166 A1* | 10/2010 | Boraiah | A61B 17/3421 606/232 |
| 2011/0028796 A1* | 2/2011 | Blinman | A61B 17/3421 600/227 |
| 2011/0144440 A1* | 6/2011 | Cropper | A61B 17/3421 600/203 |
| 2011/0306841 A1* | 12/2011 | Lozman | A61B 17/1684 600/204 |
| 2013/0030457 A1* | 1/2013 | Tan | A61B 17/3421 606/185 |
| 2013/0310773 A1* | 11/2013 | Richard | A61B 17/3423 604/278 |
| 2014/0323809 A1* | 10/2014 | Bonadio | A61B 17/3423 600/208 |
| 2014/0371537 A1* | 12/2014 | Marczyk | A61B 17/3462 600/204 |
| 2015/0038997 A1* | 2/2015 | Malkowski | A61B 17/3417 606/148 |
| 2015/0073223 A1* | 3/2015 | Pravongviengkham | A61B 17/0218 600/207 |
| 2015/0216514 A1* | 8/2015 | Weisbrod | A61B 17/0218 606/232 |
| 2016/0354113 A1* | 12/2016 | Spenciner | A61B 17/3421 |
| 2017/0189061 A1* | 7/2017 | Weisbrod | A61B 17/0401 |
| 2017/0245888 A1* | 8/2017 | Buyda | A61B 17/3421 |
| 2018/0310975 A1* | 11/2018 | Haufe | A61B 17/1659 |
| 2019/0290255 A1 | 9/2019 | Pravongviengkham et al. | |
| 2019/0307486 A1* | 10/2019 | Buyda | A61B 17/3421 |

FOREIGN PATENT DOCUMENTS

| | | |
|---|---|---|
| EP | 0880939 A1 | 12/1998 |
| EP | 3549537 A1 | 10/2019 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9721461 A1 | 6/1997 |
| WO | 9912602 A1 | 3/1999 |
| WO | 0126724 A2 | 4/2001 |
| WO | 02096307 A2 | 12/2002 |
| WO | 2004032756 A2 | 4/2004 |

* cited by examiner

RETENTION ANCHOR FOR SURGICAL ACCESS DEVICES

FIELD

The present disclosure relates generally to surgical access devices. In particular, the present disclosure relates to a retention anchor for fixing a surgical access device in tissue.

BACKGROUND

In minimally invasive surgical procedures, including endoscopic and laparoscopic surgeries, a surgical access device permits the introduction of a variety of surgical instruments into a body cavity or opening. A surgical access device (e.g., a cannula or an access port) is introduced through an opening in tissue (e.g., a naturally occurring orifice or an incision) to provide access to an underlying surgical site in the body. The opening is typically made using an obturator having a blunt or sharp tip that may be inserted through a passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall, and is then removed to permit introduction of surgical instruments through the surgical access device to perform the surgical procedure.

Minimally invasive surgical procedures, including both endoscopic and laparoscopic procedures, permit surgery to be performed on organs, tissues, and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through a cannula into the abdominal cavity to perform one or more surgical tasks. The cannula may incorporate a seal to establish a substantially fluid tight seal about the laparoscopic instrument to preserve the integrity of the pneumoperitoneum. The cannula, which is subjected to the pressurized environment, e.g., the pneumoperitoneum, may include an anchor mechanism to prevent the cannula from backing out of the opening in the abdominal wall, for example, during withdrawal of the laparoscopic instrument from the cannula. The cannula may also include a retention mechanism to prevent the cannula for being over-inserted into the abdominal wall, for example, during insertion of the laparoscopic instrument into the cannula. The holding force of the retention mechanism may be impacted during a surgical procedure by bodily fluids and/or surgical lubricants at the surgical site, manipulation of the cannula within the tissue during the surgical procedure, and/or multiple instrument insertions and withdrawals through the cannula.

SUMMARY

This disclosure generally relates to a retention anchor for securing a surgical access device within tissue. The retention anchor provides a counter force during insertion and/or articulation of surgical instruments through the surgical access device. In aspects in which the surgical access device includes an anchor mechanism, the retention anchor is utilized in conjunction with the anchor mechanism to limit longitudinal movement of the surgical access device relative to the tissue (e.g., retropulsion and over-insertion) during, for example, receipt, manipulation, and/or withdrawal of surgical instruments or specimens therethrough.

The retention anchor includes an annular body and a wiper disposed at a distal end of the annular body. The retention anchor provides a stable holding force on a surgical access device and reduces variations in forces that the retention anchor experiences during a surgical procedure. For example, the wiper minimizes the introduction of fluids (e.g., bodily fluids and/or surgical lubricants) into the retention anchor which can otherwise challenge (e.g., decrease) the holding force of the retention anchor.

In one aspect, the disclosure provides a surgical access assembly including a cannula and a retention anchor. The cannula includes an elongated shaft and the retention anchor is movably positioned along the elongated shaft. The retention anchor includes an annular body and a wiper disposed at a distal end of the annular body. The annular body includes a proximally-facing surface, a distally-facing surface, an outer side surface, and an inner side surface. The inner side surface defines a channel for reception and passage of the elongated shaft therethrough and the proximally-facing surface defines a proximal opening into the channel. The wiper extends radially inwardly of the inner side surface and defines a distal opening into the channel for establishing a sealed relation about the elongated shaft. The distal opening having a smaller diameter than the proximal opening.

The inner side surface of the annular body may frictionally engage the elongated shaft of the cannula. The inner surface of the annular body may include ridges disposed in longitudinally spaced relation relative to each other. Each ridge may include a flat surface and an angled surface. The flat surface may be proximally facing, and the angled surface may be distally facing.

The wiper may include a disc-shaped body having a flat proximal facing surface and a flat distal facing surface. The wiper may have a uniform thickness and the ridges may have a variable thickness, and the thickness of the wiper may be less than a minimal thickness of the ridges. The wiper may extend radially from the inner side surface of the annular body into the channel.

The annular body and the wiper may be monolithically formed from a common material.

In another aspect, the disclosure provides a retention anchor for a surgical access device. The retention anchor includes an annular body and a wiper disposed at a distal end of the annular body. The annular body includes a proximally-facing surface, a distally-facing surface, an outer side surface, and an inner side surface. The inner side surface defines a channel for reception and passage of the elongated shaft therethrough, and the proximally-facing surface defines a proximal opening into the channel. The wiper extends radially inwardly of the inner side surface and defines a distal opening into the channel for establishing a sealed relation about the elongated shaft. The distal opening has a smaller diameter than the proximal opening.

The details of one or more aspects of the disclosure are set forth in the accompanying drawings and the description below. Other features, objects, and advantages of the aspects described in this disclosure will be apparent from the description and drawings, and from the claims.

DETAILED DESCRIPTION

Figure 1:
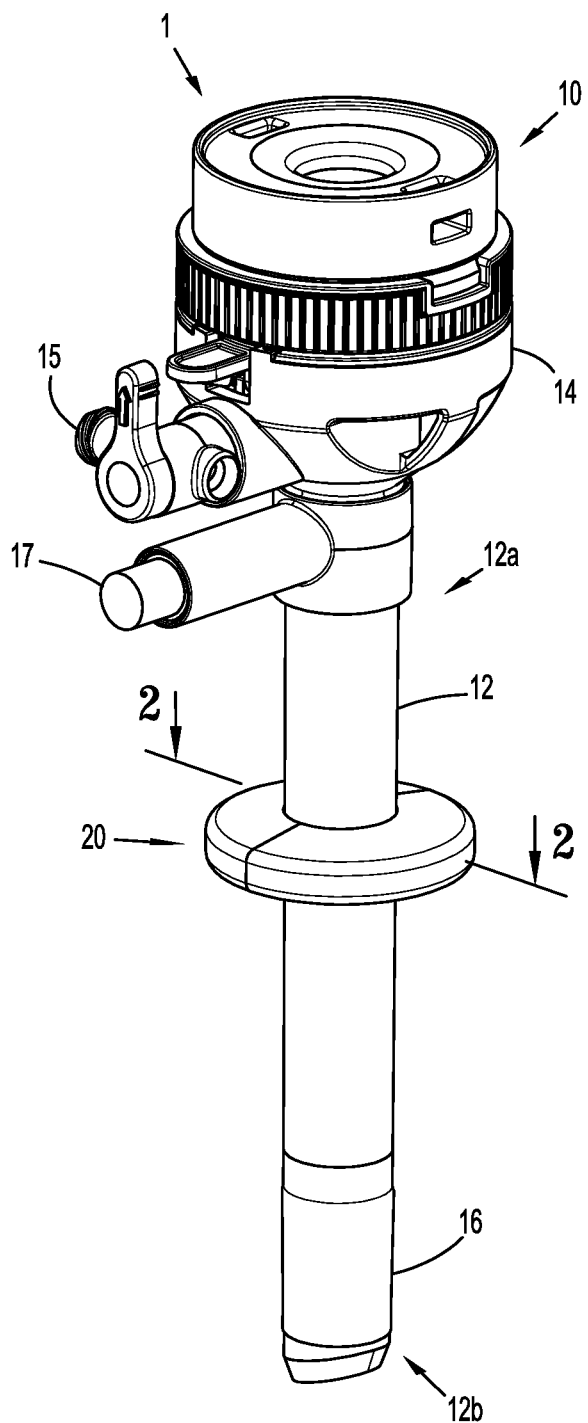
FIG. 1 is a perspective view of a surgical access assembly including a cannula and a retention anchor in accordance with an aspect of the disclosure.

Aspects of the disclosure are described hereinbelow with reference to the accompanying drawings; however, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Like reference numerals refer to similar or identical elements throughout the description of the figures. Throughout this description, the term "proximal" refers to a portion of a structure, or component thereof, that is closer to a user, and the term "distal" refers to a portion of the structure, or component thereof, that is farther from the user.

FIG. 1 illustrates a surgical access assembly 1 including a surgical access device or cannula 10 and a retention anchor 20. The cannula 10 generally includes an elongated shaft 12 supporting an instrument housing 14 on a proximal or first end portion 12a thereof and an expandable anchor 16 (e.g., an inflatable anchor, such as a balloon, or a contractable anchor, such as a collapsible flange or a kinked mesh) on a distal or second end portion 12b thereof. The expandable anchor 16 secures the cannula 10 against an inner surface of tissue, such as an abdominal wall (see e.g., FIG. 4).

The retention anchor 20 is supported on the elongated shaft 12 of the cannula 10. The retention anchor 20 is releasably engageable with the elongated shaft 12, and slidable therealong to adjust the position of the retention anchor 20 on the elongated shaft 12. The retention anchor 20 secures the cannula 10 against an outer surface of the tissue (see e.g., FIG. 4) and stabilizes the cannula 10 relative to the tissue.

Generally, the cannula 10 is employed during surgery (e.g., laparoscopic surgery) to access a surgical site and may, in various aspects, provide for the sealed access of surgical instruments into an insufflated body cavity, such as an abdominal cavity. The instrument housing 14 of the cannula 10 may include an insufflation port 15 that provides insufflation fluid (e.g., gases) into the body cavity, seals and/or valves (not shown) that allow surgical instrumentation to be inserted into the body cavity while preventing the escape of the insufflation fluid therefrom, and an anchor inflation port 17 which is in fluid communication with the expandable anchor 16 to expand and/or contract the expandable anchor 16.

The cannula 10 is usable with an obturator (not shown). The obturator generally includes an elongated body supporting a tip on a distal end thereof. The tip can have a bladed or non-bladed (e.g., blunt) penetrating distal end that can be used to incise or separate tissue of a body wall so that the cannula 10 can be introduced therethrough. The cannula 10 and the obturator may be capable of being selectively connected together. For example, the obturator may be inserted into and through the cannula 10 until a handle housing of the obturator engages, e.g., selectively locks into, the instrument housing 14 of the cannula 10. In this initial position, the cannula 10 and the obturator, which together form a trocar assembly, are employed to tunnel through a body wall, e.g., an abdominal wall, either by making a new passage through the body wall or by passing through an existing opening through the body wall. Once the trocar assembly has tunneled through the body wall, the obturator is removed, leaving the cannula 10 in place, e.g., in an incision created by the trocar assembly.

For a detailed description of the structure and function of exemplary surgical access devices suitable for use with a retention anchor of the present disclosure, reference may be made to U.S. Pat. Nos. 7,691,089; 8,926,508; and 10,299,778, the entire contents of each of which are hereby incorporated by reference herein.

Figure 2:
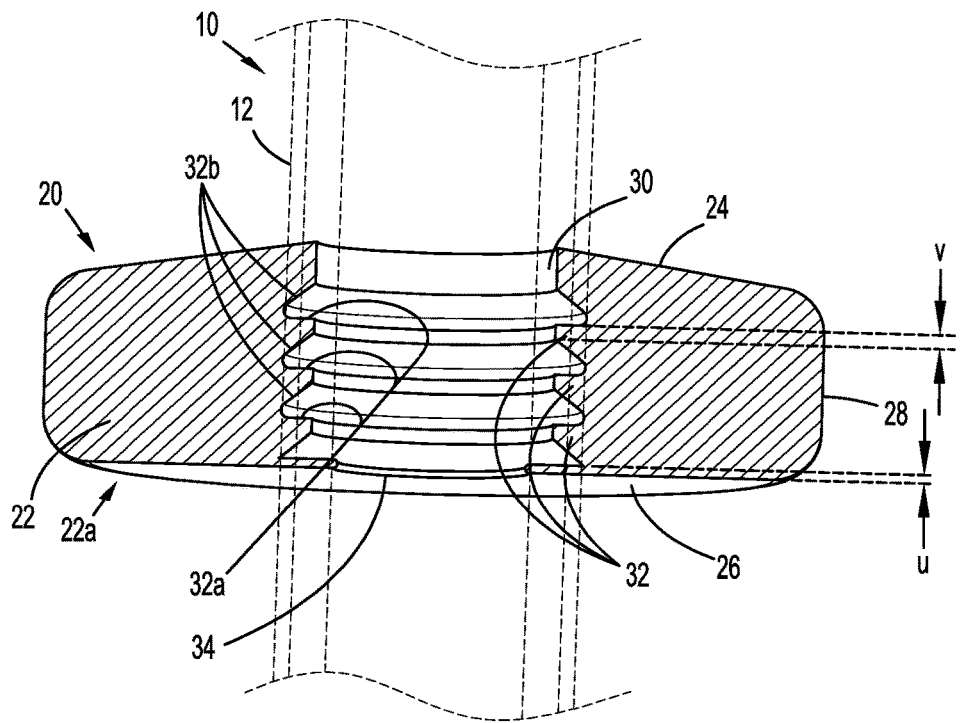
FIG. 2 is cross-sectional view of the surgical access assembly of FIG. 1, taken along section line 2-2 of FIG. 1.
Figure 3:
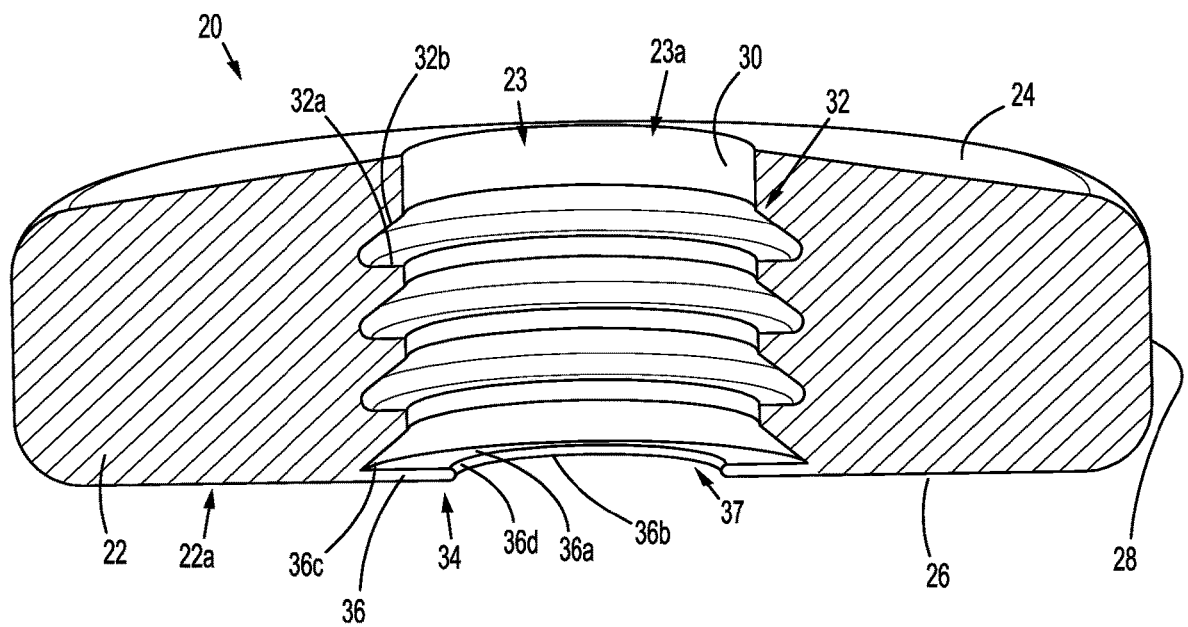
FIG. 3 is a cross-sectional view of the retention anchor of FIG. 1.

Turning now to FIGS. 2 and 3, in conjunction with FIG. 1, the retention anchor 20 includes an annular body 22 having a first or proximally-facing surface 24, a second or distally-facing surface 26, an outer side surface 28, and an inner side surface 30. The outer and inner side surfaces 28, 30 extend between and interconnect the first and second surfaces 24, 26. The inner side surface 30 defines a channel or passageway 23 extending longitudinally through the annular body 22 that is sized and shaped to accommodate the elongated shaft 12 of the cannula 10 in a friction fit manner. A proximal opening 23a into the channel 23 is defined through the first surface 24.

The inner side surface 30 of the annular body 22 includes ridges 32 to enhance the grip of the annular body 22 about the elongated shaft 12 of the cannula 10 and to limit movement of the retention anchor 20 relative to the cannula 10. The ridges 32 are disposed in longitudinally spaced relation relative to each other within the channel 23. The ridges 32 are also longitudinally spaced from the proximal opening 23a. Each ridge 32 includes a flat surface 32a and an angled surface 32b defined in the inner side surface 30 of the annular body 22. The angled surfaces 32b are distally-facing surfaces that accommodate flexing of the ridges 32 when a distal force is applied to the retention anchor 20 to permit distal movement of the retention anchor 20 relative to the cannula 10. The flat surfaces 32a are proximally-facing surfaces that limit flexing of the ridges 32 when a proximal force is applied to the retention anchor 20 to prevent or minimize proximal movement of the retention anchor 20 relative to the cannula 10. In this manner, once the retention anchor 20 is secured to the elongated shaft 12 of the cannula 10, the retention anchor 20 may be moved distally along the elongate shaft 12 of the cannula 10 to abut tissue (see e.g., FIG. 4), and proximal movement is limited to ensure that the surgical access assembly 1 remains fixed relative to the tissue throughout a surgical procedure.

It should be understood that in addition or as an alternative to the ridges 32, the inner side surface 30 of the annular body 22 may include protrusions, bumps, projections, or other textured finishes to aid in frictionally retaining the retention anchor 20 on the elongated shaft 12 of the cannula 10 while allowing movement of the retention anchor 20 relative to the elongated shaft 12.

The retention anchor 20 includes a wiper 34 at a distal end 22a of the annular body 22. The wiper 34 includes a disc-shaped body 36 having a flat proximal facing surface 36a, a flat distal facing surface 36b, an outer terminal edge 36c, and an inner terminal edge 36d defining a distal opening 37 into the channel 23. The distal opening 37 has a smaller diameter than the proximal opening 23a of the channel 23 and is concentric with the proximal opening 23a. The wiper 34 creates a seal around the elongated shaft 12 of the cannula 10 when the elongated shaft 12 is disposed therethrough while allowing for longitudinal movement of the elongated shaft 12 relative thereto.

The wiper 34 extends from the inner side surface 30 of the annular body 22 radially into the channel 23, distal to the ridges 32. The flat distal facing surface 36b of the wiper 34 is aligned with the second surface 26 of the annular body 22 to form a continuous and smooth distal end 22a of the annular body 22. It is envisioned that the wiper 34 may be sized such that the flat proximal facing surface 36a of the wiper 34 may be secured to the second surface 26 of the annular body 22 with the distal opening 37 disposed radially inwardly of the inner side surface 30 defining the channel 23. It is also envisioned that the wiper 34 can extend from the inner side surface 30 of the annular body 22 into the channel 23 proximal to the distal end 22a of the annular body 22 (e.g., the wiper 34 need not be at a distal-most end of the annular body 22), so long as the wiper 34 is disposed distal to the ridges 32.

The wiper 34 is thin compared to the ridges 32. The wiper 34 has a uniform thickness "U" and the ridges 32 have a variable thickness, where a minimal thickness "V" of the ridge 32, which is disposed adjacent to the inner side surface 30 of the annular body 22, is greater than the thickness "U" of the wiper 34. The minimal thickness "V" of the ridge 32 may be at least two times the thickness "U" of the wiper 34 and, in some aspects, the minimal thickness "V" of the ridge 32 is about three times the thickness "U" of the wiper 34. The thickness and configuration of the wiper 34 accommodates flexing of the wiper 34 about the elongated shaft 12 of the cannula 10 in a sealed relation therewith during proximal and distal movement of the wiper 34 relative to the elongated shaft 12, and warrants no tear and/or yield of the material forming the wiper 34. In this manner, once the retention anchor 20 is secured to the cannula 10, the wiper 34 limits the introduction of fluids into the retention anchor 20 (e.g., fluids on the elongated shaft 12 of the cannula 10 and/or from the tissue at the surgical site).

The annular body 22 and the wiper 34 are each formed from a flexible material, such as rubber, plastic, or other suitable polymer (e.g., elastomers). The annular body 22 and the wiper 34 may be monolithically formed from the same or common material (e.g., a rubber or an elastomer), or the annular body 22 and the wiper 34 may be separate components formed from the same or different materials that are fixedly secured together by, for example, solvent bonding, overmolding, using adhesives, etc.

Figure 4:
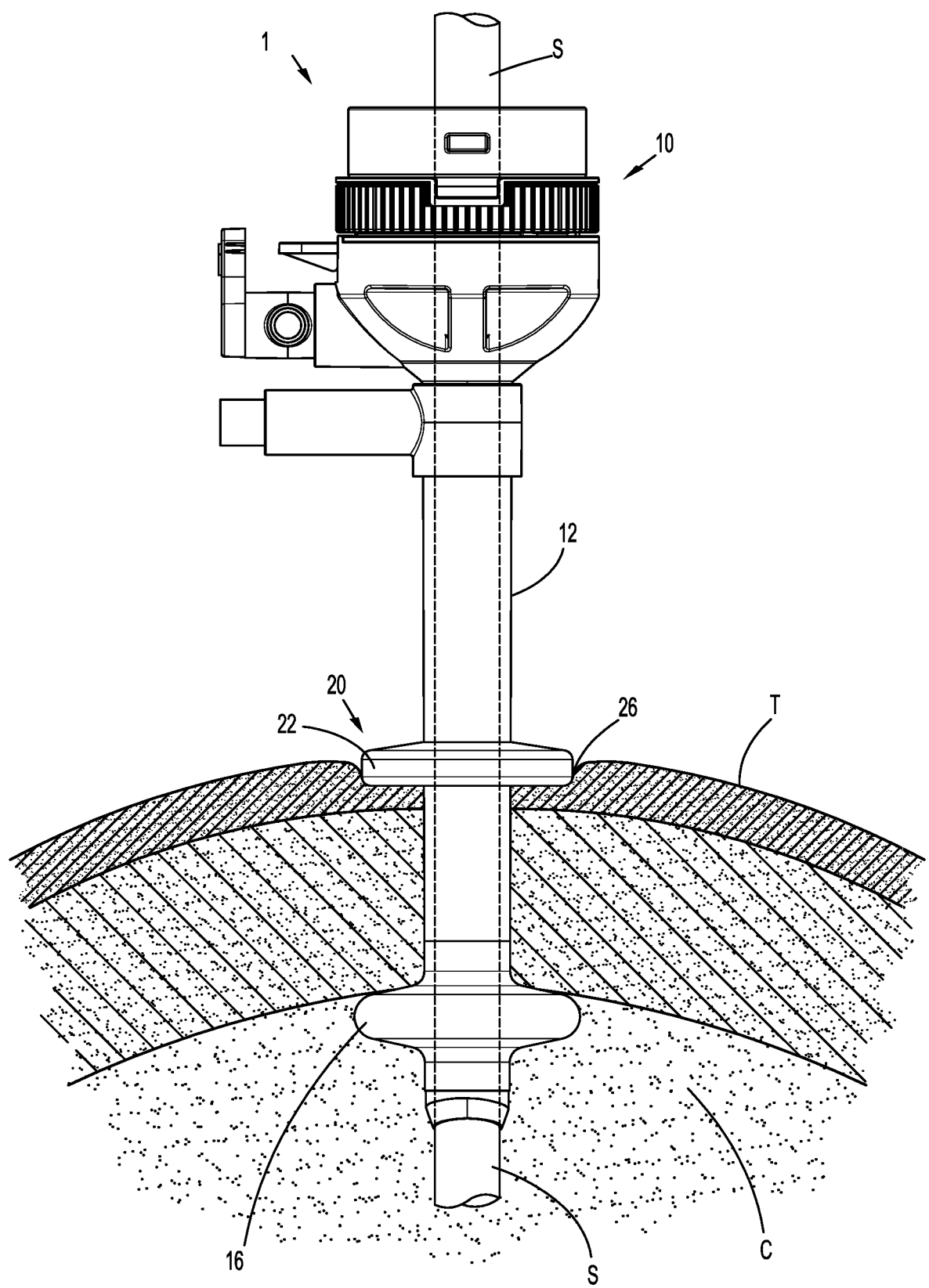
FIG. 4 is a side view of the surgical access assembly of FIG. 1, shown secured to tissue.

FIG. 4 illustrates the surgical access assembly 1 disposed within tissue "T," e.g., an abdominal wall. The retention anchor 20 is secured to the cannula 10 prior to introducing the cannula 10 into the tissue "T" (e.g., the retention anchor 20 may be pre-installed on the cannula 10 during manufacture or may be placed on the cannula 10 prior to use in the operating room). The elongated shaft 12 of the cannula 10 is received through the tissue "T" (e.g., by utilizing an obturator (not shown) to facilitate entry of the cannula 10 through the tissue "T"), and the expandable anchor 16 is inflated within a body cavity "C" to prevent the cannula 10 from being withdrawn through the tissue "T." The retention anchor 20 is slid distally along the elongated shaft 12 of the cannula 10 until the retention anchor 20 abuts or presses on the tissue "T." The tissue "T" is thus sandwiched between the expandable anchor 16 and the retention anchor 20 to prevent the cannula 10 from being withdrawn from or over-inserted into the tissue "T." In this manner, the surgical access assembly 1 is secured to the tissue "T" and longitudinal movement of the cannula 10 relative to the tissue "T" is prevented or minimized throughout insertion, withdrawal, and/or manipulation of a surgical instrument "S" or a specimen through the cannula 10.

During the surgical procedure, the retention anchor 20 may be subjected to fluids (e.g., bodily fluids from the surgical site and/or surgical lubricants utilized during the surgical procedure) which can reduce the frictional forces of the retention anchor 20 on the elongated shaft 12 of the cannula 10. As the second surface 26 of the annular body 22 is positioned adjacent to the tissue "T," the wiper 34 is also positioned adjacent to the tissue "T" and, as discussed above, is in sealing engagement with the elongated shaft 12 of the cannula 10. Accordingly, the wiper 34 limits fluids from entering the channel 23 of the annular body 22 and impacting the holding force achieved by the ridges 32 of the annular body 22 on the elongated shaft 12 of the cannula 10. Thus, the configuration of the retention anchor 20 provides a stable holding force independent of variations in forces due to fluids.

Following the surgical procedure, the expandable anchor 16 is deflated to permit the withdrawal of the cannula 10 from the tissue "T." The retention anchor 20 may remain secured to and disposed about the elongated shaft 12 of the cannula 10 during withdrawal of the cannula 10, or may be moved (e.g., slid proximally along the elongated shaft 12).

It should be understood that the surgical access assembly 1 is suitable for use in a variety of surgical procedures, such as surgical procedures performed within the peritoneum or extraperitoneally (e.g., hernial procedures).

While aspects of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be effected by one skilled in the art without departing from the scope or spirit of the disclosure. Therefore, the above description should not be construed as limiting, but merely as exemplifications of aspects of the disclosure. Thus, the scope of the disclosure should be determined by the appended claims and their legal equivalents, rather than by the examples given.

What is claimed is:

1. A surgical access assembly comprising:
   a cannula including an elongated shaft; and
   a retention anchor movably positioned along the elongated shaft, the retention anchor comprising:
      an annular body including a proximally-facing surface disposed at a proximal end of the annular body, a distally-facing surface disposed at a distal end of the annular body, an outer side surface, and an inner side surface, the inner side surface defining a channel for reception and passage of the elongated shaft therethrough, the proximally-facing surface defining a proximal opening into the channel at the proximal end of the annular body;
      a plurality of ridges extending radially inward from the inner side surface, each ridge of the plurality of ridges having a flat surface and an angled surface, the angled surface defining an acute angle with respect to the flat surface; and
      a wiper disposed at the distal end of the annular body, the wiper extending radially inward, the wiper having a flat distal-facing surface aligned with the distally-facing surface of the annular body to define a distal opening into the channel for establishing a sealed relation about the elongated shaft, the distal opening having a smaller diameter than the proximal opening.

2. The surgical access assembly of claim 1, wherein the inner side surface of the annular body frictionally engages the elongated shaft of the cannula.

3. The surgical access assembly of claim 2, wherein each ridge of the plurality of ridges is longitudinally spaced relative to an adjacent ridge of the plurality of ridges.

4. The surgical access assembly of claim 3, wherein the flat surface of each ridge of the plurality of ridges is proximally facing.

5. The surgical access assembly of claim 4, wherein the angled surface of each ridge of the plurality of ridges is distally facing.

6. The surgical access assembly of claim 1, wherein the wiper includes a disc-shaped body having a flat proximal facing surface and a flat distal facing surface.

7. The surgical access assembly of claim 1, wherein the wiper has a uniform thickness and each ridge of the plurality of ridges has a variable thickness, and wherein the uniform thickness of the wiper is less than a minimal thickness of the variable thickness of each ridge of the plurality of ridges.

8. The surgical access assembly of claim 1, wherein the annular body and the wiper are monolithically formed from a common material.

9. The surgical access assembly of claim 1, wherein the wiper extends radially inward from the inner side surface of the annular body into the channel.

10. A retention anchor for a surgical access device, the retention anchor comprising:
   an annular body including a proximally-facing surface disposed at a proximal end of the annular body, a distally-facing surface disposed at a distal end of the annular body, an outer side surface, and an inner side surface, the inner side surface defining a channel for reception and passage of the elongated shaft therethrough, the proximally-facing surface defining a proximal opening into the channel at the proximal end of the annular body;
   a plurality of ridges extending radially inward from the inner side surface, each ridge of the plurality of ridges having a flat surface and an angled surface, the angled surface defining an acute angle with respect to the flat surface; and
   a wiper disposed at the distal end of the annular body, the wiper extending radially inward, the wiper having a flat distal-facing surface aligned with the distally-facing surface of the annular body to define a distal opening into the channel for establishing a sealed relation about the elongated shaft, the distal opening having a smaller diameter than the proximal opening.

11. The retention anchor of claim 10, wherein each ridge of the plurality of ridges is longitudinally spaced relative to an adjacent ridge of the plurality of ridges.

12. The retention anchor of claim 11, wherein the flat surface of each ridge of the plurality of ridges is proximally facing.

13. The retention anchor of claim 12, wherein the angled surface of each ridge of the plurality of ridges is distally facing.

14. The retention anchor of claim 10, wherein the wiper includes a disc-shaped body having a flat proximal facing surface and a flat distal facing surface.

15. The retention anchor of claim 10, wherein the wiper has a uniform thickness and each ridge of the plurality of ridges has a variable thickness, and wherein the uniform thickness of the wiper is less than a minimal thickness of the variable thickness of each ridge of the plurality of ridges.

16. The retention anchor of claim 10, wherein the annular body and the wiper are monolithically formed from a common material.

17. The retention anchor of claim 10, wherein the wiper extends radially inward from the inner side surface of the annular body into the channel.

* * * * *